(12) United States Patent
Ohban

(10) Patent No.: US 8,449,114 B2
(45) Date of Patent: May 28, 2013

(54) FUNDUS IMAGING APPARATUS

(75) Inventor: Hideyuki Ohban, Kawaguchi (JP)

(73) Assignee: Canon Kabushiki Kaisha, Tokyo (JP)

( * ) Notice: Subject to any disclaimer, the term of this patent is extended or adjusted under 35 U.S.C. 154(b) by 58 days.

(21) Appl. No.: 13/216,400

(22) Filed: Aug. 24, 2011

(65) Prior Publication Data

US 2012/0050677 A1 Mar. 1, 2012

(30) Foreign Application Priority Data

Aug. 31, 2010 (JP) ................................ 2010-194751

(51) Int. Cl.
*A61B 3/14* (2006.01)
*A61B 3/10* (2006.01)

(52) U.S. Cl.
USPC ............................ 351/206; 351/205; 351/221

(58) Field of Classification Search
USPC ................................................ 351/200–246
See application file for complete search history.

(56) References Cited

U.S. PATENT DOCUMENTS

| | | | | |
|---|---|---|---|---|
| 7,837,329 B2 | 11/2010 | Yoshino et al. | ................ | 351/206 |
| 8,057,039 B2 * | 11/2011 | Akita et al. | .................... | 351/206 |
| 8,246,169 B2 * | 8/2012 | Sumiya | ......................... | 351/206 |
| 2009/0244483 A1 | 10/2009 | Yoshino et al. | ................ | 351/206 |

FOREIGN PATENT DOCUMENTS

| | | |
|---|---|---|
| JP | 04-317628 A | 11/1992 |
| JP | 08-275921 A | 10/1996 |
| JP | 2005-143679 A | 6/2005 |
| JP | 2009-240625 A | 10/2009 |
| JP | 4430378 B2 | 3/2010 |

* cited by examiner

*Primary Examiner* — Mohammed Hasan
(74) *Attorney, Agent, or Firm* — Fitzpatrick, Cella, Harper & Scinto

(57) ABSTRACT

Provided is a fundus imaging apparatus which achieves reduction of a load on an examiner by facilitating understanding of an operation of switching from a fundus imaging mode to an anterior ocular segment imaging mode, comprising: an imaging unit for taking an image of an eye to be inspected; a focusing unit for achieving a substantially conjugate relationship between the eye to be inspected and the imaging unit; a diopter adjustment unit for adjusting a diopter when the eye to be inspected is myopic or hyperopic; an imaging selecting unit capable of selecting the fundus imaging mode or the anterior ocular segment imaging mode; a diopter adjustment switching unit for switching the diopter adjustment unit in accordance with the selected imaging mode; and a drive unit for driving the focusing unit in accordance with the selected imaging mode.

7 Claims, 3 Drawing Sheets

FUNDUS IMAGING APPARATUS

BACKGROUND OF THE INVENTION

1. Field of the Invention

The present invention relates to a fundus imaging apparatus, and more particularly, to a fundus imaging apparatus capable of imaging an anterior ocular segment of an eye to be inspected.

2. Description of the Related Art

Conventionally, there has been known a fundus camera capable of observing and imaging a fundus and an anterior ocular segment of an eye to be inspected. A fundus camera disclosed in Japanese Patent Application Laid-Open No. H04-317628 supports imaging of the anterior ocular segment as well by spacing the eye to be inspected away from the fundus camera, and moving a focus lens for focusing between an image of the eye to be inspected and an imaging plane in a hyperopic direction when imaging the anterior ocular segment.

In a case where an examiner such as an ophthalmologist uses the fundus camera as described above for imaging the anterior ocular segment, the examiner first switches a diopter adjustment lens to a hyperopia lens, and moves the focus lens in the hyperopic direction. Then, the examiner greatly moves the fundus camera toward the examiner side. Finally, the examiner performs alignment for imaging the anterior ocular segment of the subject, and then performs imaging of the anterior ocular segment.

As described above, in the fundus camera capable of imaging the anterior ocular segment as well, there is a problem in that the switching from the fundus imaging mode to the anterior ocular segment imaging mode is extremely complicated, hard to understand, and time consuming. To address this problem, in a fundus camera disclosed in Japanese Patent Application Laid-Open No. H08-275921, in order to image the anterior ocular segment, an imaging optical system for the anterior ocular segment is separately provided, which allows imaging of the anterior ocular segment. However, the apparatus increases in size and manufacturing cost.

Further, in an ophthalmologic imaging apparatus disclosed in Japanese Patent No. 4,430,378, a moving amount per unit rotational angle of a focus knob is changed between the case of imaging the fundus and the case of imaging the anterior ocular segment. Accordingly, in the case of imaging the anterior ocular segment, the focus lens can be moved greatly, and hence it is expected that the period of time required for the switching from the fundus imaging mode to the anterior ocular segment imaging mode can be reduced to a certain extent. However, it is hard to say that the examiner's operation is reduced.

SUMMARY OF THE INVENTION

The present invention has been made in view of the above-mentioned problems, and it is therefore an object of the present invention to provide a fundus imaging apparatus capable of reducing a load on an examiner and reducing a period of time required for switching from a fundus imaging mode to an anterior ocular segment imaging mode by facilitating understanding of a switching operation and simplifying the switching operation.

A fundus imaging apparatus according to the present invention includes: an imaging unit for receiving reflected light from an eye to be inspected through an optical system to take an image of the eye to be inspected; a focusing unit for achieving a substantially conjugate relationship between the eye to be inspected and the imaging unit; a diopter adjustment unit for adjusting a diopter when the eye to be inspected is myopic or hyperopic; an imaging selecting unit capable of selecting one of a fundus imaging mode, in which a fundus of the eye to be inspected is imaged, and an anterior ocular segment imaging mode, in which an anterior ocular segment of the eye to be inspected is imaged; a diopter adjustment switching unit for switching the diopter adjustment unit in accordance with the one of the fundus imaging mode and the anterior ocular segment imaging mode selected by the imaging selecting unit; and a drive unit for driving the focusing unit in accordance with the one of the fundus imaging mode and the anterior ocular segment imaging mode selected by the imaging selecting unit.

According to the present invention, the load on the examiner can be reduced and the period of time required for the switching from the fundus imaging mode to the anterior ocular segment imaging mode can be reduced by facilitating understanding of the switching operation.

Further features of the present invention will become apparent from the following description of exemplary embodiments with reference to the attached drawings.

DESCRIPTION OF THE EMBODIMENTS

Hereinbelow, exemplary embodiments of the present invention are described with reference to the attached drawings. In the embodiments of the present invention, description is given by using a non-mydriatic fundus camera as a fundus imaging apparatus.

(First Embodiment)

Figure 1:
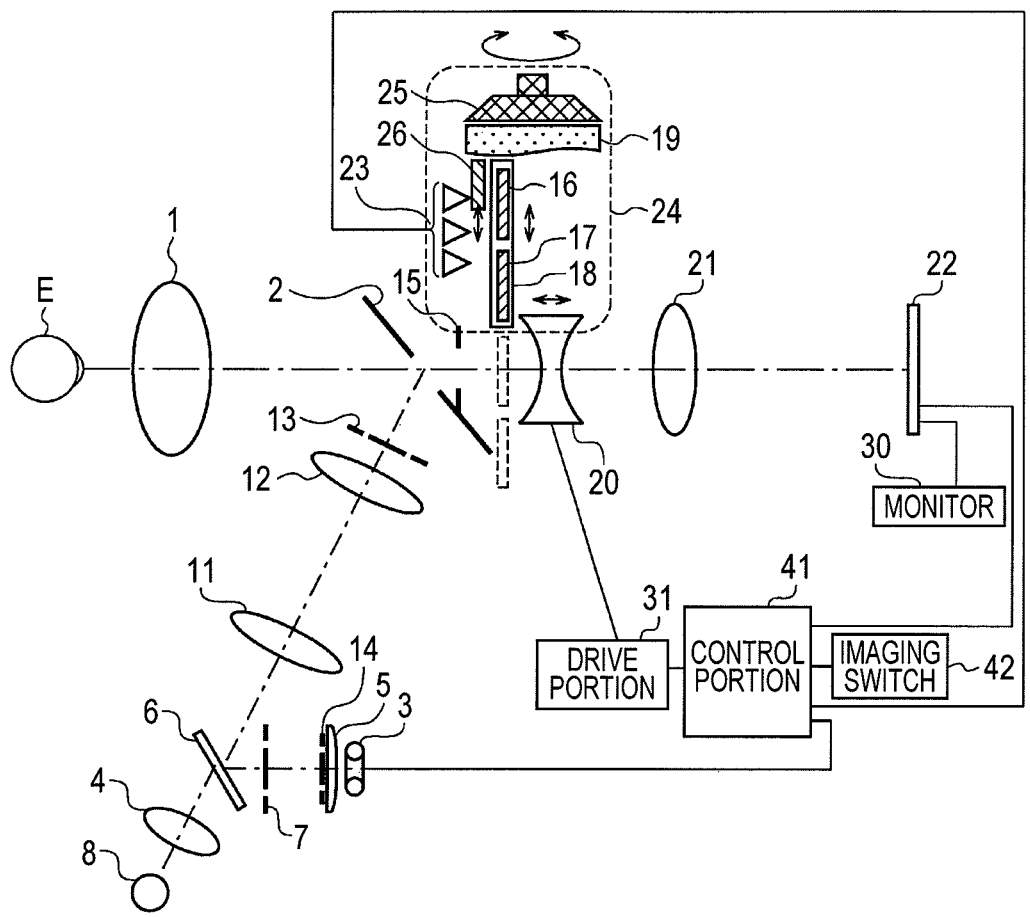
FIG. 1 is a diagram illustrating a configuration of a non-mydriatic fundus camera according to embodiments of the present invention.

FIG. 1 is a diagram illustrating a configuration of the non-mydriatic fundus camera.

The fundus camera includes a lens 4, a relay lens 11, a relay lens 12, and a cornea stop 13 having a ring-like opening portion, which are arranged in order on an optical path ranging from a near-infrared LED 8 serving as an observation illumination light source to an objective lens 1 through a perforated mirror 2. The lens 4 has a function of enhancing effectiveness of utilizing light emitted from the near-infrared LED 8. Further, the cornea stop 13 separates an illumination light beam from an imaging light beam so as to prevent adverse light (reflected light) from a cornea of an eye E to be inspected due to the illumination light beam from entering an imaging stop 15.

Further, the fundus camera includes a lens 5, a pupil stop 14 having a ring-like opening portion, and a crystalline lens stop 7 having a ring-like opening portion, which are arranged in order on an optical path ranging from a xenon tube 3 serving as an imaging light source to a mirror 6 arranged between the relay lens 11 and the lens 4. The xenon tube 3 is a stroboscopic light source for emitting flashes of visible light, and a visible light LED may be used instead. The lens 5 has a function of enhancing effectiveness of utilizing light emitted from the xenon tube 3. Further, the pupil stop 14 is arranged substantially at a conjugate position with the eye E to be inspected. The crystalline lens stop 7 separates the illumination light beam from the imaging light beam so as to prevent adverse light (reflected light) from a crystalline lens of the eye E to be inspected due to the illumination light beam from entering the imaging stop 15.

Such an optical system ranging from the near-infrared LED 8 serving as the observation illumination light source and the xenon tube 3 serving as the imaging light source to the objective lens 1 through the perforated mirror 2 constitutes an illumination optical system.

In the rear of the perforated mirror 2, the imaging stop 15, a focus lens 20 serving as a focusing unit, an imaging lens 21, and an imaging portion 22 are arranged. The imaging portion 22 is an imaging element such as a CCD, and is capable of receiving light of an image of the eye to be inspected. Further, the imaging portion 22 has a sensitivity that covers a visible light range and an invisible (near-infrared) light range, and is capable of outputting a moving image and a still image.

Such an optical system ranging from the objective lens 1 to the imaging portion 22 constitutes an observation/imaging optical system.

Further, the fundus camera includes a control portion 41 for controlling the entire system, a drive portion 31, an imaging switch 42, and a monitor 30. The above-mentioned imaging portion 22, drive portion 31, and imaging switch 42 are each connected to the control portion 41.

The drive portion 31 moves the focus lens 20 in an optical axis direction based on an instruction of the control portion 41. The imaging switch 42 is a switch to be pressed by the examiner when the examiner instructs the control portion 41 to perform imaging. Further, the monitor 30 is connected to the imaging portion 22, and the examiner therefore displays an output image signal of a moving image or a still image taken by the imaging portion 22.

In the fundus camera of this embodiment, the examiner can switch between a fundus imaging mode and an anterior ocular segment imaging mode through a switching operation portion serving as an imaging selecting unit. First, a case where the fundus imaging mode is selected in the fundus camera is described.

[Fundus Imaging Mode]

In the case where the fundus imaging mode is selected, the near-infrared LED 8 emits light to irradiate the fundus of the eye E to be inspected through the illumination optical system. Reflected light from the fundus of the eye E to be inspected is imaged on the imaging portion 22 through the observation/imaging optical system. The reflected light from the fundus is focused on the imaging portion 22 by the control portion 41 moving the focus lens 20 in the optical axis direction through the drive portion 31 in accordance with an operation performed by the examiner through a focus operation portion (not shown). Further, the examiner performs alignment of the fundus of the eye E to be inspected by operating an alignment operation portion (not shown) provided to the fundus camera.

Further, there are cases where the subject is highly myopic and where the subject is highly hyperopic conversely. In those cases, focus cannot be achieved within the movable range of the focus lens 20.

The fundus camera of this embodiment includes a diopter adjustment switching portion 24 for inserting a diopter adjustment portion 18 into the observation/imaging optical system. The diopter adjustment switching portion 24 includes a high-myopia diopter adjustment lens 17 and a high-hyperopia diopter adjustment lens 16 as the diopter adjustment portion 18.

In the case where the subject is highly myopic, the diopter adjustment switching portion 24 inserts the high-myopia diopter adjustment lens 17 into the observation/imaging optical system in accordance with an operation performed by the examiner through a switching operation portion 25.

On the other hand, in the case where the subject is highly hyperopic, the diopter adjustment switching portion 24 inserts the high-hyperopia diopter adjustment lens 16 into the observation/imaging optical system in accordance with an operation performed by the examiner through the switching operation portion 25.

The examiner performs the above-mentioned operations through the focus lens operation member and the switching operation portion 25 while observing the fundus of the eye E to be inspected, which is displayed on the monitor 30. Further, the examiner presses the imaging switch 42 after performing the alignment and focusing. In the fundus camera, the xenon tube 3 emits light and the fundus of the eye E to be inspected is imaged on the imaging portion 22 through the observation/imaging optical system, with the result that the image of the fundus of the eye E to be inspected can be obtained.

[Anterior Ocular Segment Imaging Mode]

In the case where the anterior ocular segment imaging mode is selected, the near-infrared LED 8 emits light to irradiate the anterior ocular segment of the eye E to be inspected through the illumination optical system.

At this time, the diopter adjustment switching portion 24 inserts the high-hyperopia diopter adjustment lens 16 into the observation/imaging optical system in accordance with an operation of selecting the anterior ocular segment imaging mode, which is performed by the examiner through the switching operation portion 25.

Further, the diopter adjustment switching portion 24 of the fundus camera includes a diopter adjustment detecting portion 23 for detecting a state of the diopter adjustment portion 18, and a state of each of the fundus imaging mode and the anterior ocular segment imaging mode. The diopter adjustment detecting portion 23 detects a current imaging mode that is selected through the operation performed by the examiner through the switching operation portion 25. In this case, the diopter adjustment detecting portion 23 detects that the anterior ocular segment imaging mode is selected. The diopter adjustment detecting portion 23 transmits, to the control portion 41, a signal indicating that the anterior ocular segment imaging mode is selected, and the control portion 41 therefore moves the focus lens 20 in a hyperopic direction through the drive portion 31.

After that, the examiner performs operations through the focus operation member and the alignment operation portion while observing the anterior ocular segment of the eye E to be inspected, which is displayed on the monitor 30, to thereby perform focusing and alignment of the anterior ocular segment. Further, the examiner presses the imaging switch 42 after finishing the alignment and focusing. In the fundus camera, the xenon tube 3 emits light and the anterior ocular segment of the eye E to be inspected is imaged on the imaging portion 22 through the observation/imaging optical system, with the result that the image of the anterior ocular segment of the eye E to be inspected can be obtained.

Next, a mechanism for selecting, by the examiner, the anterior ocular segment imaging mode through the switching operation portion 25 of the diopter adjustment switching portion 24 is described in detail.

Figure 2:
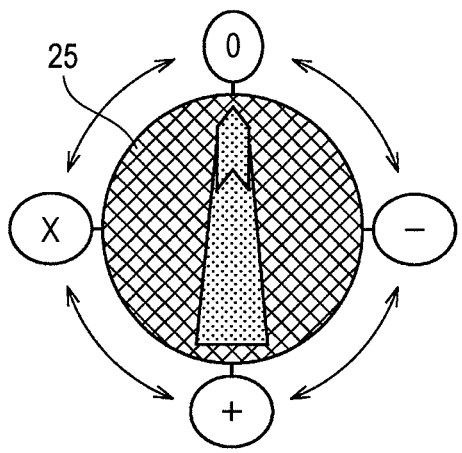
FIG. 2 is a view of an appearance of a switching selecting portion according to the embodiments of the present invention.

The switching operation portion 25 of the diopter adjustment switching portion 24 is a rotary knob as illustrated in FIG. 2, and is rotatable in the arrow directions. The examiner adjusts the switching operation portion 25 to "0" in the case where the eye E to be inspected of the subject is nearly emmetropic, "−" in the case where the eye E to be inspected of the subject is highly myopic, "+" in the case where the eye E to be inspected of the subject is highly hyperopic, and "X" in the case where the anterior ocular segment imaging mode is selected. The switching operation portion 25 is rotatable clockwise and counterclockwise. Note that, the symbols for identifying the imaging mode and the like are not limited to the above-mentioned symbols, and may be characters instead. Thus, the identification format is not limited.

Further, as illustrated in FIG. 1, the switching operation portion 25 has a diopter switching cam 19 coupled thereto, and the diopter switching cam 19 rotates in synchronization with the switching operation portion 25. The diopter switching cam 19 has a cam mechanism, and inserts and removes the high-hyperopia diopter adjustment lens 16 and the high-myopia diopter adjustment lens 17 held by the diopter adjustment portion 18 into and from the observation/imaging optical system in accordance with the rotational position of the diopter switching cam 19.

Figure 3:
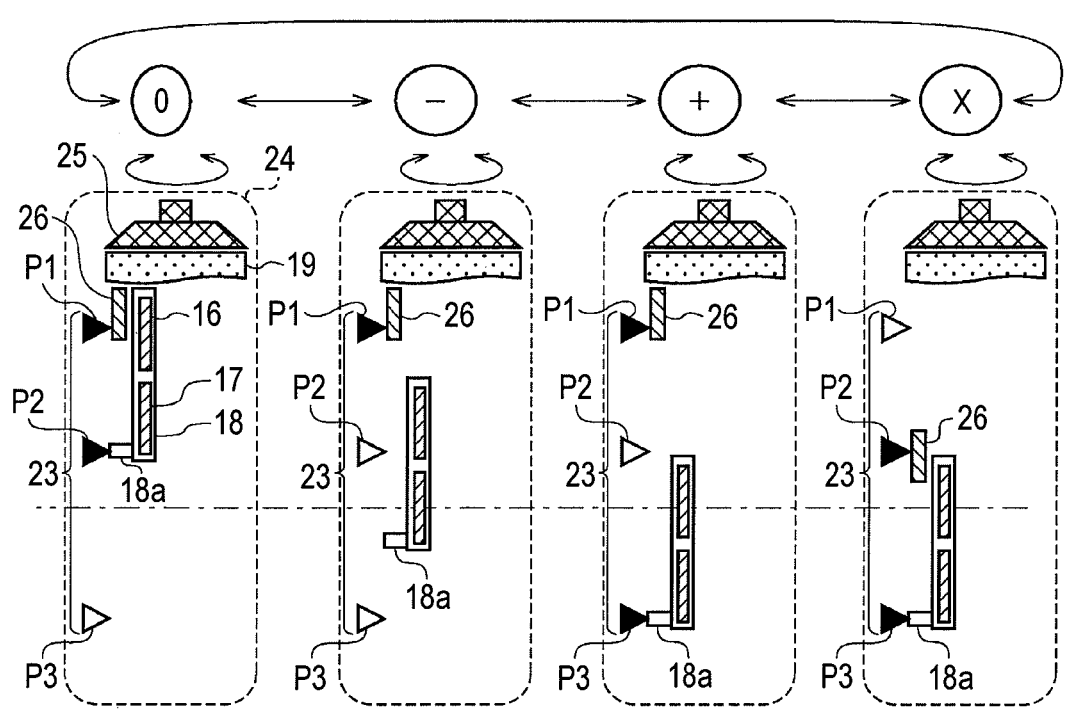
FIG. 3 is a schematic diagram illustrating a configuration of a diopter adjustment switching portion according to the embodiments of the present invention.

Further, the diopter switching cam 19 has a fundus/anterior ocular imaging switching lever 26 coupled thereto. The diopter switching cam 19 moves the fundus/anterior ocular imaging switching lever 26 in accordance with the rotational position of the diopter switching cam 19. Through the movement of the diopter adjustment portion 18 and the fundus/anterior ocular imaging switching lever 26, the diopter adjustment detecting portion 23 detects the state of the diopter adjustment lens, and at the same time, detects the state of each of the fundus imaging mode and the anterior ocular segment imaging mode. Referring to FIG. 3, a method of detecting the imaging mode and the like by the diopter adjustment detecting portion 23 is described later.

Next, an operation to be performed in the fundus camera in a case where the examiner operates the switching operation portion 25 to rotate and changes the selection from the state of the fundus imaging mode to the state of the anterior ocular segment imaging mode is described.

First, the examiner operates the switching operation portion 25 to rotate clockwise or counterclockwise, to thereby adjust the switching operation portion 25 to "X" indicating the anterior ocular segment imaging mode.

Then, the diopter switching cam 19 coupled to the switching operation portion 25 performs rotational motion in synchronization with the switching operation portion 25.

The diopter adjustment portion 18 abuts against a cam surface of the diopter switching cam 19. Accordingly, through the rotation of the diopter switching cam 19, the diopter adjustment portion 18 performs translational motion to switch the state of the diopter adjustment lens.

Further, the fundus/anterior ocular imaging switching lever 26 abuts against the cam surface of the diopter switching cam 19. Accordingly, through the rotation of the diopter switching cam 19, the fundus/anterior ocular imaging switching lever 26 performs translational motion to switch to the state in which the anterior ocular segment imaging mode is detected by the diopter adjustment detecting portion 23.

Now, referring to the schematic diagram of FIG. 3, a mechanism for detecting the imaging of the myopic or hyperopic eye, or the imaging mode by the diopter adjustment detecting portion 23 is described specifically. As illustrated in FIG. 3, the diopter adjustment detecting portion 23 includes sensors P1 to P3 such as photoelectric sensors arranged in parallel.

When the imaging mode is the fundus imaging mode and the adjustment lens is not inserted because of the imaging of the nearly emmetropic eye (in the case of "0"), the fundus/anterior ocular imaging switching lever 26 is positioned at the sensor P1, and a detection-subject portion 18a formed on the diopter adjustment portion 18 is positioned at the sensor P2. Therefore, the diopter adjustment detecting portion 23 detects that "P1 is effective", "P2 is effective", and "P3 is ineffective". The term "effective" herein refers to a state in which the sensor detects an object. Further, in FIG. 3, when each of the sensors P1 to P3 is effective, such a state is represented by a black triangle, and when each of the sensors P1 to P3 is ineffective, such a state is represented by a white triangle.

When the imaging mode is the fundus imaging mode and the high-myopia diopter adjustment lens 17 is inserted because of the imaging of the highly myopic eye (in the case of "−"), the fundus/anterior ocular imaging switching lever 26 is positioned at the sensor P1, and the detection-subject portion 18a is positioned between the sensor P2 and the sensor P3. Therefore, the diopter adjustment detecting portion 23 detects that "P1 is effective", "P2 is ineffective", and "P3 is ineffective".

When the imaging mode is the fundus imaging mode and the high-hyperopia diopter adjustment lens 16 is inserted because of the imaging of the highly hyperopic eye (in the case of "+"), the fundus/anterior ocular imaging switching lever 26 is positioned at the sensor P1, and the detection-subject portion 18a is positioned at the sensor P3. Therefore, the diopter adjustment detecting portion 23 detects that "P1 is effective", "P2 is ineffective", and "P3 is effective".

When the imaging mode is the anterior ocular segment imaging mode (in the case of "X"), the fundus/anterior ocular imaging switching lever 26 is positioned at the sensor P2, and the detection-subject portion 18a is positioned at the sensor P3. Therefore, the diopter adjustment detecting portion 23 detects that "P1 is ineffective", "P2 is effective", and "P3 is effective".

In other words, the diopter adjustment detecting portion 23 detects the sensors P1 to P3 in the following detection pattern.

Fundus imaging mode, imaging of nearly emmetropic eye: P1: effective, P2: effective, P3: ineffective Fundus imaging mode, imaging of highly myopic eye: P1: effective, P2: ineffective, P3: ineffective Fundus imaging mode, imaging of highly hyperopic eye: P1: effective, P2: ineffective, P3: effective Anterior ocular segment imaging mode: P1: ineffective, P2: effective, P3: effective Through the rotational motion of the diopter switching cam 19, the diopter adjustment portion 18 and the fundus/anterior ocular imaging switching lever 26 impose a change in the diopter adjustment detecting portion 23 in the above-mentioned detection pattern.

The diopter adjustment detecting portion 23 detects the state of the diopter adjustment lens, and the state of each of the fundus imaging mode and the anterior ocular segment imaging mode in accordance with the pattern. The diopter adjustment detecting portion 23 notifies the control portion 41 of the state of the imaging mode, and therefore the control portion 41 moves the focus lens 20 through the drive portion 31 in accordance with the imaging mode. For example, when the examiner changes the imaging mode from the fundus imaging mode to the anterior ocular segment imaging mode, the control portion 41 moves the focus lens 20 in the hyperopic direction through the drive portion 31. In this case, the three sensors P1 to P3 are used to detect the state of the diopter adjustment lens and the state of the imaging mode, but the present invention is not limited to this case. Sensors may be arranged at the respective rotational positions of the switching operation portion 25, to thereby detect the state of the diopter adjustment lens and the state of the imaging mode.

In this manner, the examiner only operates the switching operation portion 25 and adjusts the switching operation portion 25 to the specified position of the anterior ocular segment imaging mode. Thus, in the fundus camera, the diopter adjustment lens suitable to image the anterior ocular segment is set and the focus lens 20 is moved to the suitable position.

After that, the examiner operates the alignment operation portion to perform the focusing and alignment operations for the anterior ocular segment of the eye E to be inspected while observing the monitor 30. Further, the examiner presses the imaging switch 42 after performing the alignment and focusing. In the fundus camera, the anterior ocular segment of the eye E to be inspected is imaged, with the result that the image of the anterior ocular segment of the eye E to be inspected can be obtained.

According to this embodiment, the switching operation portion 25 that is capable of selecting the fundus imaging mode or the anterior ocular segment imaging mode is provided. Thus, the examiner can realize the fundus imaging mode or the anterior ocular segment imaging mode through distinct selection, with the result that the fundus imaging and the anterior ocular segment imaging is clearly distinguished from each other. Further, the state of each of the diopter adjustment switching portion 24 and the focus lens 20 is switched to a suitable state in accordance with the imaging mode selected by the switching operation portion 25, and thus the switching operation of the examiner can be performed simply.

Further, at the time of the anterior ocular segment imaging, in the diopter adjustment switching portion 24, it is necessary to use the high-hyperopia diopter adjustment lens 16 as the diopter adjustment portion 18. In this embodiment, the diopter adjustment switching portion 24 is identical with the switching operation portion 25, and hence there is no need to separately provide any drive system for diopter adjustment switching (switching for hyperopia) at the time of the anterior ocular segment imaging. As a result, the configuration for switching to the anterior ocular segment imaging can be simplified.

(Second Embodiment)

Figure 4:
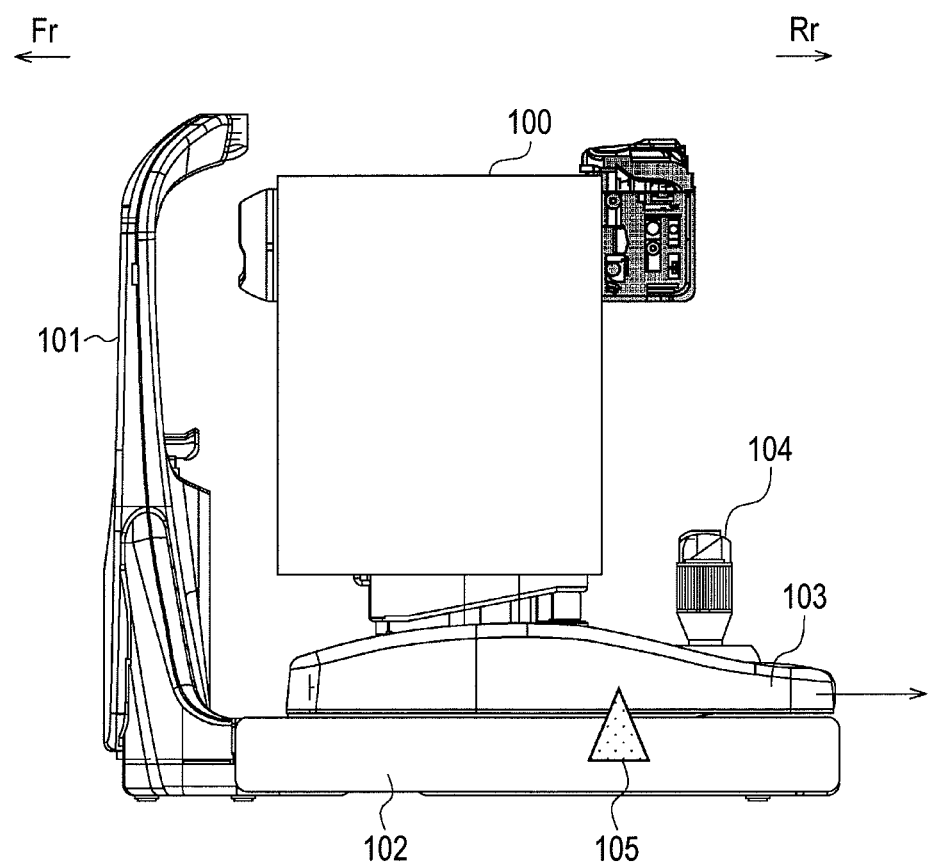
FIG. 4 is an overall view of the non-mydriatic fundus camera.

FIG. 4 is a view illustrating an overall configuration of the non-mydriatic fundus camera. A configuration of an optical main body 100 is the same as the configuration of FIG. 1, and description thereof is therefore omitted herein. In FIG. 4, the front side of the fundus camera is represented by "Fr", and the rear side thereof is represented by "Rr".

The fundus camera includes a fixed base 102 having a face receiving portion 101 fixed to the front side thereof, the face receiving portion 101 supporting the face of the subject, and a movable stage 103 movable on the fixed base 102 from front to back and from side to side, and having the optical main body 100 mounted thereto. Further, the fundus camera includes an alignment operation portion 104 for operating the movable stage 103.

When the examiner operates the alignment operation portion 104, the movable stage 103 and the optical main body 100 move from front to back and from side to side in association with each other.

In the case of performing the anterior ocular segment imaging, as described in the first embodiment, the diopter switching cam 19 inserts the high-hyperopia diopter adjustment lens 16 of the diopter adjustment portion 18 into the observation/imaging optical system, and the control portion 41 moves the focus lens 20 toward the hyperopic side. In this embodiment, in a case where the focus is not achieved on the anterior ocular segment of the eye E to be inspected even through the above-mentioned operation, the examiner can operate the alignment operation portion 104 to move the movable stage 103 toward the examiner side.

Further, as illustrated in FIG. 4, the fundus camera of this embodiment includes, in any one of the fixed base 102 and the movable stage 103, an alignment detecting portion 105 for detecting the position of the movable stage 103 in the back-and-forth direction, and a selection drive portion (not shown) as an imaging selection drive unit. The alignment detecting portion 105 and the selection drive portion are each electrically connected to the control portion 41 illustrated in FIG. 1. The selection drive portion rotates the diopter switching cam 19.

Under a state in which the fundus imaging mode is selected as the imaging mode, at the time of the anterior ocular segment imaging, the examiner needs to greatly move the movable stage 103 toward the examiner side (rearward) in order to image the anterior ocular segment. When the examiner operates the alignment operation portion 104 to move the movable stage 103 toward the examiner side, the alignment detecting portion 105 detects the position of the movable stage 103 after the movable stage 103 moves by a predetermined distance, and transmits a signal (detection information) to the control portion 41. The control portion 41 moves the focus lens 20 toward the hyperopic side through the drive portion 31 so that the anterior ocular segment can be imaged. Further, the control portion 41 rotates the diopter switching cam 19 through the selection drive portion to insert the high-hyperopia diopter adjustment lens 16 into the observation/imaging optical system. After that, the examiner presses the imaging switch 42 to image the anterior ocular segment of the eye E to be inspected in the fundus camera, with the result that the image of the anterior ocular segment of the eye E to be inspected can be obtained.

In this embodiment, the alignment detecting portion 105 serving as a movable stage detecting unit for detecting the position of the movable stage 103 is provided, and based on the output therefrom, the state of each of the diopter adjustment switching portion 24 and the focus lens 20 is switched to a suitable state. Thus, the anterior ocular segment imaging can be performed only by operating the movable stage 103, and as a result, the switching between the fundus imaging and the anterior ocular segment imaging can be simplified.

As described above, according to the first and second embodiments, the fundus imaging mode and the anterior ocular segment imaging mode can be selected clearly and distinctly. In addition, the switching operation from the fundus imaging mode to the anterior ocular segment imaging mode can be minimized, with the result that the anterior ocular segment imaging can be performed comfortably.

Hereinabove, the present invention has been described with reference to various exemplary embodiments, but the present invention is not limited only to those embodiments, and modifications and the like may be made within the scope of the present invention.

For example, the second embodiment has described the case where the examiner operates the alignment operation portion 104 to move the movable stage 103 toward the examiner side in order to image the anterior ocular segment, but the present invention is not limited to this case. For example, the same configuration may be employed for a case where the examiner operates the alignment operation portion 104 to move the movable stage 103 toward the subject side when the examiner images the fundus after imaging the anterior ocular segment. Specifically, the alignment detecting portion 105 detects the position of the movable stage 103 after the movable stage 103 moves toward the subject side by a predetermined distance, and transmits a signal to the control portion 41. The control portion 41 moves the focus lens 20 toward the myopic side through the drive portion 31 so that the fundus can be imaged. Further, the control portion 41 rotates the diopter switching cam 19 through the selection drive portion to the position of the fundus imaging mode.

Further, the present invention is also implemented by executing the following processing. Specifically, in this processing, software (program) for implementing the functions of the above-mentioned embodiments is supplied to a system or an apparatus via a network or various kinds of storage medium, and a computer (or CPU, MPU, etc.) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-194751, filed Aug. 31, 2010, which is hereby incorporated by reference herein in its entirety.

What is claimed is:

1. A fundus imaging apparatus, comprising:
   an imaging unit for receiving reflected light from an eye to be inspected through an optical system to take an image of the eye to be inspected;
   a focusing unit for achieving a substantially conjugate relationship between the eye to be inspected and the imaging unit;
   a diopter adjustment unit for adjusting a diopter when the eye to be inspected is myopic or hyperopic;
   an imaging selecting unit capable of selecting one of a fundus imaging mode, in which a fundus of the eye to be inspected is imaged, and an anterior ocular segment imaging mode, in which an anterior ocular segment of the eye to be inspected is imaged;
   a diopter adjustment switching unit for switching the diopter adjustment unit in accordance with the one of the fundus imaging mode and the anterior ocular segment imaging mode selected by the imaging selecting unit; and
   a drive unit for driving the focusing unit in accordance with the one of the fundus imaging mode and the anterior ocular segment imaging mode selected by the imaging selecting unit.

2. A fundus imaging apparatus according to claim 1,
   wherein the diopter adjustment switching unit moves in association with the imaging selecting unit, and
   wherein the diopter adjustment unit is inserted into and removed from the optical system in accordance with a position selected by the imaging selecting unit.

3. A fundus imaging apparatus according to claim 2, wherein, when the anterior ocular segment imaging mode is selected by the imaging selecting unit, the diopter adjustment switching unit inserts a hyperopia diopter adjustment lens held by the diopter adjustment unit into the optical system.

4. A fundus imaging apparatus according to claim 1,
   wherein, when the fundus imaging mode is selected by the imaging selecting unit, the drive unit drives the focusing unit toward a myopic side, and
   wherein, when the anterior ocular segment imaging mode is selected by the imaging selecting unit, the drive unit drives the focusing unit toward a hyperopic side.

5. A fundus imaging apparatus according to claim 2,
   wherein the diopter adjustment switching unit comprises a cam mechanism,
   wherein the fundus imaging apparatus further comprises:
     a switching lever positionally changeable in association with the cam mechanism; and
     a detecting unit for detecting a position of the switching lever and a position of the diopter adjustment unit, and
   wherein the drive unit drives the focusing unit based on detection information obtained through the detection performed by the detecting unit.

6. A fundus imaging apparatus according to claim 1, further comprising:
   a movable stage having the imaging unit mounted thereto, the movable stage being capable of moving the imaging unit toward one of a myopic side and a hyperopic side with respect to the eye to be inspected; and
   a movable stage detecting unit for detecting a position of the movable stage,
   wherein the drive unit drives the focusing unit in accordance with the position of the movable stage detected by the movable stage detecting unit.

7. A fundus imaging apparatus according to claim 6, further comprising an imaging selection drive unit for driving the imaging selecting unit,
   wherein the imaging selection drive unit drives the imaging selecting unit to select the one of the fundus imaging mode and the anterior ocular segment imaging mode in accordance with the position of the movable stage detected by the movable stage detecting unit.

* * * * *